United States Patent
Holle (10) Patent No.: US 9,375,583 B2
(45) Date of Patent: Jun. 28, 2016

(54) MEDICAL SYSTEM LEAD ADAPTER PROVIDING FOR CUSTOMIZED STIMULATION PATTERN FOR A SECONDARY LEAD

(71) Applicant: Medtronic, Inc., Minneapolis, MN (US)

(72) Inventor: Mark J. Holle, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/391,210

(22) PCT Filed: Jan. 25, 2013

(86) PCT No.: PCT/US2013/023192
§ 371 (c)(1),
(2) Date: Oct. 8, 2014

(87) PCT Pub. No.: WO2013/147984
PCT Pub. Date: Oct. 3, 2013

(65) Prior Publication Data
US 2015/0080988 A1    Mar. 19, 2015

Related U.S. Application Data

(60) Provisional application No. 61/618,650, filed on Mar. 30, 2012.

(51) Int. Cl.
*A61N 1/375* (2006.01)
*H01R 31/06* (2006.01)
*A61N 1/05* (2006.01)
*H01R 24/58* (2011.01)

(52) U.S. Cl.
CPC ............... *A61N 1/3752* (2013.01); *A61N 1/05* (2013.01); *H01R 31/06* (2013.01); *A61N 1/0551* (2013.01); *H01R 24/58* (2013.01); *H01R 2201/12* (2013.01)

(58) Field of Classification Search
None
See application file for complete search history.

(56) References Cited

U.S. PATENT DOCUMENTS

| | | | |
|---|---|---|---|
| 4,628,934 A | 12/1986 | Pohndorf et al. | |
| 5,443,065 A * | 8/1995 | Berghoff ............ | A61N 1/37211 439/380 |
| 5,501,703 A | 3/1996 | Holsheimer et al. | |
| 5,643,330 A | 7/1997 | Holsheimer et al. | |
| 5,895,416 A | 4/1999 | Barreras, Sr. et al. | |
| 6,004,172 A * | 12/1999 | Kerek ................... | H01R 13/10 439/879 |
| 6,587,733 B1 | 7/2003 | Cross, Jr. et al. | |
| 6,725,096 B2 * | 4/2004 | Chinn .................. | A61N 1/05 439/299 |
| 7,165,320 B2 | 1/2007 | Ishii et al. | |

(Continued)

FOREIGN PATENT DOCUMENTS

| | | |
|---|---|---|
| WO | 2004112899 A1 | 12/2004 |
| WO | 2005009534 A1 | 2/2005 |

(Continued)

*Primary Examiner* — Brian T Gedeon
(74) *Attorney, Agent, or Firm* — Shumaker & Sieffert, P.A.

(57) ABSTRACT

Medical system lead adapters distribute stimulation signals from a port of a medical device to both a primary medical lead and a secondary medical lead. The lead adapters provide for the selectable bridging of secondary lead contacts to thereby provide for customized stimulation patterns. The lead adapters may include a primary lead connector, a secondary lead connector, and a pin connector. A pin is selected to provide a particular stimulation pattern for the secondary lead and is inserted into the pin connector to thereby bridge together contacts of the pin connector that are also connected to contacts of the secondary lead connector.

21 Claims, 9 Drawing Sheets

(56) References Cited

U.S. PATENT DOCUMENTS

| | | | |
|---|---|---|---|
| 7,212,867 B2 | 5/2007 | Van Venrooij et al. | |
| 7,563,141 B2 * | 7/2009 | Alexander | A61N 1/0529 439/669 |
| 7,736,192 B2 | 6/2010 | Alexander et al. | |
| 7,914,343 B2 | 3/2011 | Alexander et al. | |
| 8,145,315 B2 * | 3/2012 | Osypka | A61N 1/056 607/116 |
| 8,774,941 B2 * | 7/2014 | Pianca | A61N 1/0553 607/117 |
| 2003/0077943 A1 | 4/2003 | Osypka | |
| 2003/0120327 A1 * | 6/2003 | Tobritzhofer | A61N 1/05 607/116 |
| 2004/0249429 A1 | 12/2004 | Tadlock | |
| 2004/0260373 A1 | 12/2004 | Ries et al. | |
| 2005/0015130 A1 | 1/2005 | Gill | |
| 2005/0272280 A1 | 12/2005 | Osypka | |
| 2006/0020291 A1 | 1/2006 | Gozani et al. | |
| 2006/0122678 A1 | 6/2006 | Olsen et al. | |
| 2006/0173262 A1 | 8/2006 | Hegland et al. | |
| 2007/0168008 A1 | 7/2007 | Olsen | |
| 2008/0208267 A1 | 8/2008 | Alexander et al. | |
| 2010/0057176 A1 | 3/2010 | Barker | |
| 2010/0274115 A1 | 10/2010 | Werder et al. | |
| 2011/0087305 A1 | 4/2011 | Zimmerman et al. | |
| 2014/0058488 A1 * | 2/2014 | Leven | A61N 1/05 607/116 |

FOREIGN PATENT DOCUMENTS

| | | |
|---|---|---|
| WO | 2008106325 A1 | 9/2008 |
| WO | 2010148379 A1 | 12/2010 |

* cited by examiner

MEDICAL SYSTEM LEAD ADAPTER PROVIDING FOR CUSTOMIZED STIMULATION PATTERN FOR A SECONDARY LEAD

TECHNICAL FIELD

Embodiments are related to leads used with medical devices that provide stimulation. More particularly, embodiments are related to adapters that allow for a primary lead and a secondary lead where a customized stimulation patterns are available for the secondary lead.

BACKGROUND

Medical systems include a medical device and attached medical leads. The medical device which is located in a location generally convenient for implantation generates stimulation signals that are then directed to a target site by the medical leads. The medical leads include contacts that receive the stimulation signals from the medical device and include conductors that extend to a distal end where electrodes are present. The electrodes then pass the stimulation signals to the body tissue at the target site.

Generally, a particular port of a medical device has a set number of electrical connectors. The proximal end of a given medical lead designed for the medical device has a number of contacts on the proximal end and electrodes on the distal end that match the number of electrical contacts of the medical device port. In some cases, it may be desirable to drive stimulation signals to two different leads using a single port of a medical device. In such a case, an adapter may be used that has a lead portion that is installed into the medical device port and has two or more ports, one port for each lead to be driven by the signal medical device port.

Typically, such an adapter may define a primary lead and a secondary lead. In one simple case, one or more secondary leads may be driven by all electrical connectors in an identical manner as the primary lead. In other more complex cases, the primary lead is driven by the most electrical contacts of the medical device while the one or more secondary leads are driven in an identical fashion by the fewest electrical connectors. One specific example is using a spinal cord stimulation paddle lead as the primary lead, where five or more electrodes are individually controlled to create a specific stimulation pattern from the paddle. In this example, a peripheral stimulation percutaneous lead may be used as the secondary lead where only two or three electrical contacts from the medical device drive the secondary lead. Adapters distribute the stimulation from the few electrical contacts of the medical device to the several electrodes of the secondary lead in a fixed, pre-determined configuration and thus produce a pre-determined stimulation pattern. As a consequence, clinicians have no way to customize the configuration and resulting stimulation pattern of the secondary lead connected to a given adapter.

SUMMARY

Embodiments address issues such as these and others by providing medical system lead adapters that allow a clinician the ability to customize the stimulation pattern for the secondary lead. Embodiments provide adapters that allow for selectably changing the connection of stimulating paths from electrical contacts that receive stimulation signals from a medical device to contacts that deliver the stimulation signals to the various contacts of the secondary lead.

Embodiments provide a medical system lead adapter that includes an input cable having a plurality of electrical conductors that establish an electrical connection with a plurality of contacts of a medical device. The adapter further includes a first output connector that receives a proximal end of a first medical lead, the output connector having a plurality of electrical contacts that establish a connection with respective ones of a plurality of contacts of the first medical lead, the plurality of electrical contacts of the first output connector being electrically connected to respective ones of a first set of the plurality of electrical conductors. The adapter includes a second output connector that receives a proximal end of a second medical lead, the output connector having a plurality of electrical contacts that establish a connection with respective ones of a plurality of contacts of the second medical lead. Additionally, the adapter includes a pin connector having a plurality of electrical contacts where at least some of the plurality of electrical contacts of the pin connector are electrically connected to respective ones of the plurality of contacts of the second output connector, a first set of the plurality of electrical contacts of the pin connector being electrically connected to respective ones of a second set of the plurality of electrical conductors. Furthermore, the adapter includes a pin present within the pin connector, the pin including a first pin conductor that electrically bridges together a first at least one electrical contact of the pin connector not in the first set to a first electrical contact from the first set of the plurality of electrical contacts of the pin connector, the pin further including a second pin conductor that electrically bridges together a second at least one electrical contact of the pin connector not in the first set to a second electrical contact from the first set of the plurality of electrical contacts of the pin connector.

Embodiments provide a medical system that includes a medical device having a plurality of electrical contacts that are given electrical potentials to provide therapy. The medical system further includes a medical system lead adapter as discussed above.

Embodiments also provide a method of providing stimulation that involves directing a first set of stimulation signals to respective electrical contacts of a first lead. The method further involves directing a second set of stimulation signals to electrical connectors of a second lead by selectably bridging the second set of stimulation signals to electrical connectors of the second lead.

DETAILED DESCRIPTION

Embodiments provide medical system lead adapters that offer customizable stimulation patterns for the secondary lead. The stimulation pattern is customizable by selectably bridging the stimulation signals destined for the secondary leads to electrical connectors of the second lead. One such way of bridging the stimulation signals provided by various embodiments is to utilize a selection of pins, with each pin having a different conductor pattern so as to create a different bridged pathway to the contacts of the secondary lead.

Figure 1:
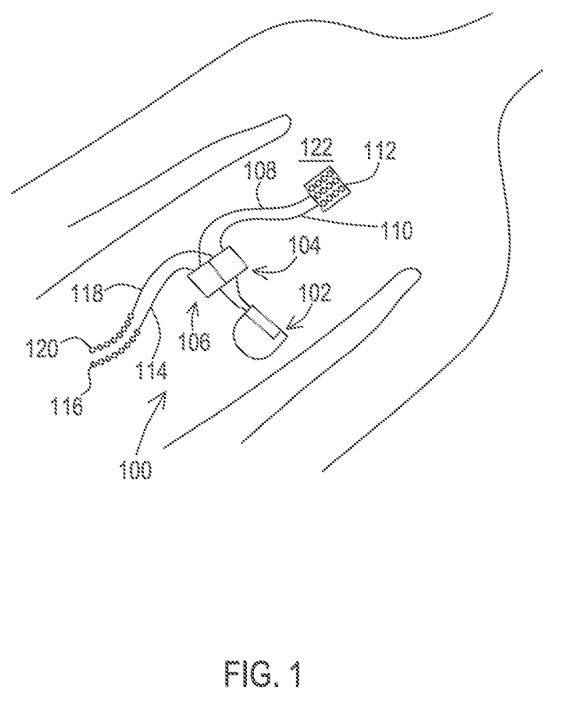
FIG. 1 shows an example of an operating environment for the various embodiments.

FIG. 1 shows a body 122 of a patient having a medical system 100 that provides stimulation therapy. In this example, the medical system 100 provides stimulation in the spinal region of the body 122. The medical system includes a medical device 102, two lead adapters 104, 106 and four medical leads 108, 110, 114, and 118. In this particular example, the leads 108, 110 are primary leads that drive one or more sets of stimulating electrodes such as those located on stimulation paddles 112 for spinal cord stimulation. Also in this particular example, the leads 114, 118 having electrodes 116, 120 are secondary leads being used for peripheral nerve stimulation in the spinal region.

As can be seen, the medical device 102 has two lead ports. Each adapter 104, 106 has a lead body that is installed in a given lead port of the medical device 102. Each adapter 104, 106 then is connected to two respective leads 108, 114 and 110, 118.

Figure 2:
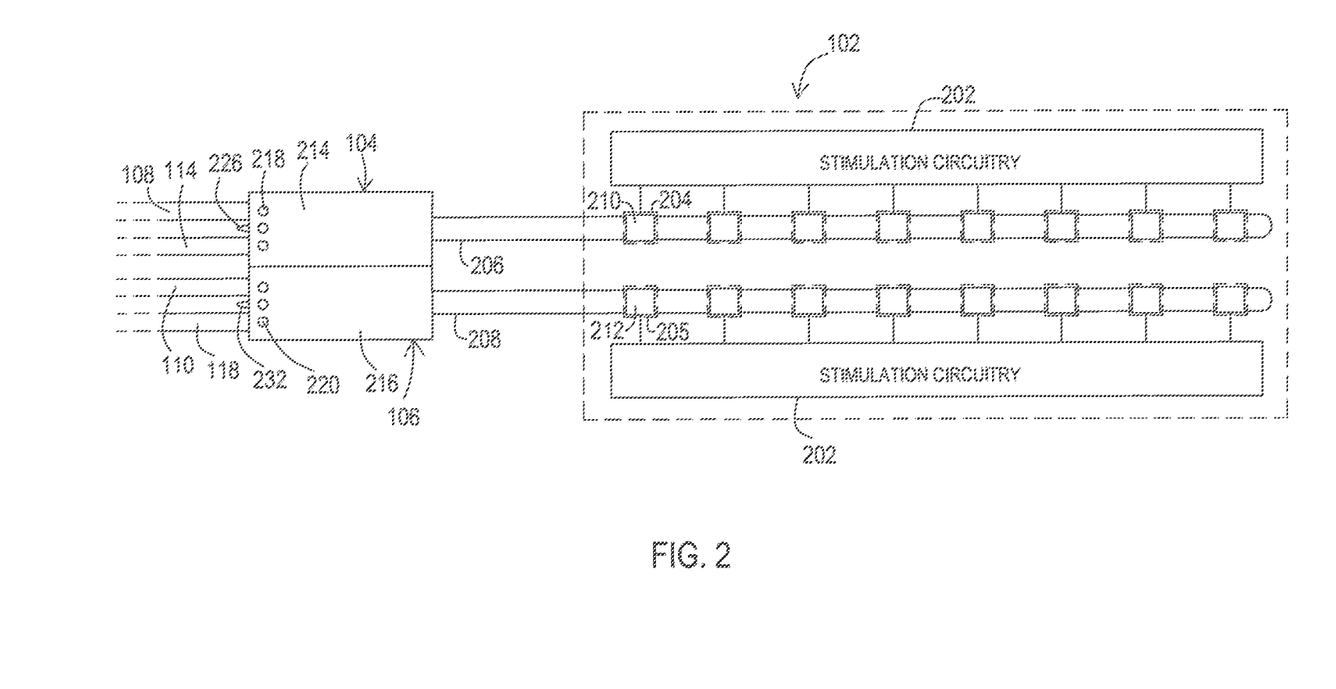
FIG. 2 shows an example of a medical system embodiment that includes multiple medical system lead adapters.

FIG. 2 shows the interconnection of the two input cables 206, 208 of the adapters 104, 106 to the lead ports of the medical device 102. The two input cables 206, 208 may take the form of lead bodies as shown. The medical device 102 has stimulation circuitry 202 that drives the sets of electrical contacts 204, 205 of the lead ports. The lead bodies of input cables 206, 208 of the adapters 104, 106 have corresponding sets of electrical contacts 210, 212 that come into physical contact with the sets of contacts to create electrical connections. Thus, conductors within the lead bodies of input cables 206, 208 early stimulation signals into the adapters 104, 106 shown with housings 214, 216. The adapters 104, 106 then distribute the stimulation signals to the medical leads 108, 114 and 110, 118 installed within the lead output connectors of the adapters 104, 106 as discussed in more detail below.

To provide for selectability and hence customization of the stimulation patterns of the secondary leads 114, 118, the adapters 104, 106 include pin connectors that receive pins 226, 232 respectively. The pins 226, 232 which are discussed in greater detail below with reference to FIGS. 3-8 provide a particular structure to electrically bridge together contacts for the secondary lead in a particular configuration.

The adapters may also include set screw structures 220 that may include a set screw block, a set screw, and a grommet. The set screw structures 220 hold the leads 108, 114, 110, 118 and pins 226, 232 in place within the adapter housings 214, 216.

Figure 3A:
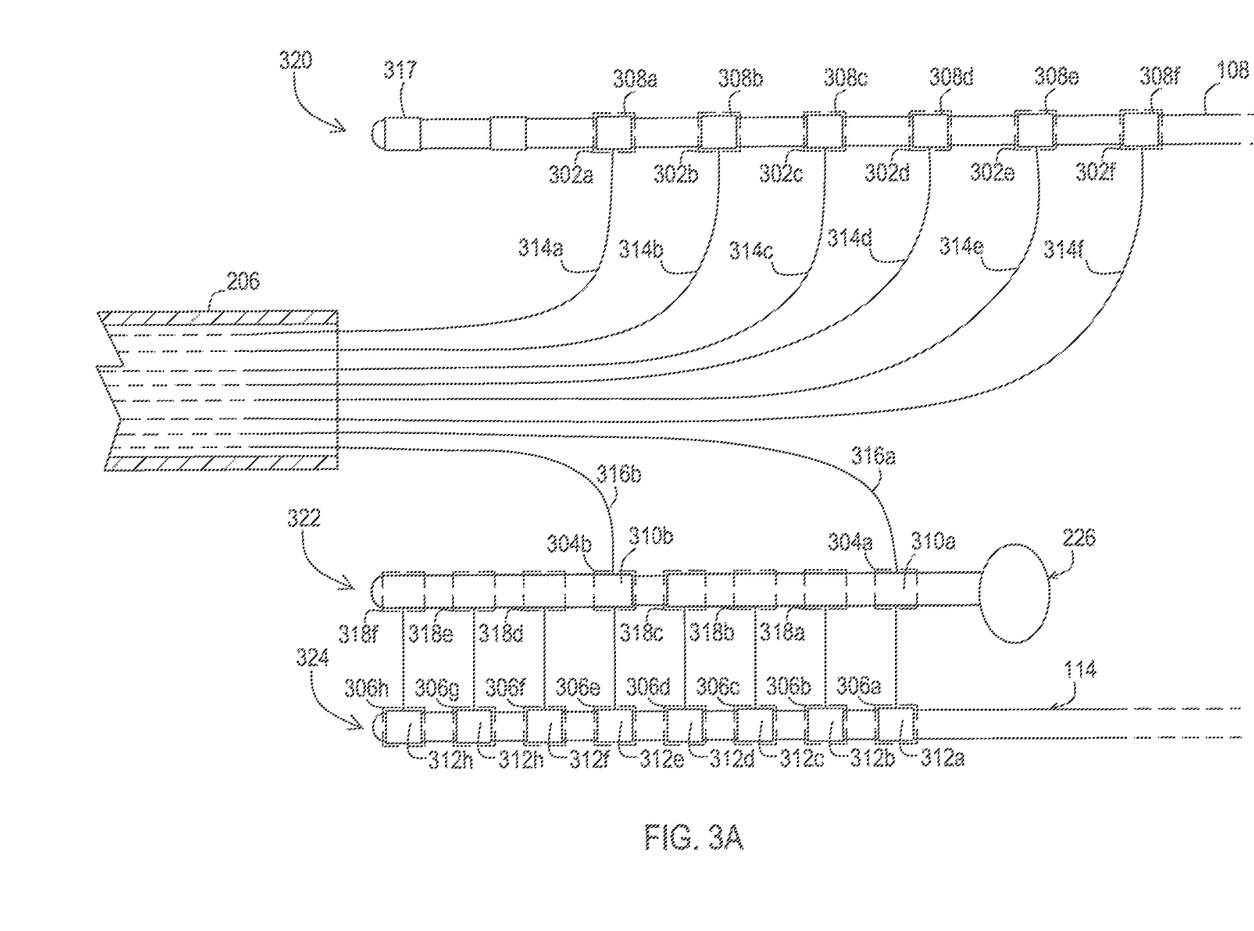
FIG. 3A shows a first example of stimulation pathways established by embodiments of a medical system lead adapter.

FIG. 3A shows an example of the pin 226 providing a particular structure that creates a particular configuration for bridging together contacts for the secondary lead 114. Initially, individual conductors 314a-314f, a first set of conductors, are directed from the lead body of input cable 206 of the adapter 104 to a set of electrical contacts 302a-302f of a primary lead output connector 320 within the adapter 104. The secondary lead 108 then has a set of electrical contacts 308a-308f that physically contact the electrical contacts 302a-302f to receive stimulation signals. In this particular example, the primary lead 108 has two additional contacts 317 which are left unconnected.

A second set of conductors 316a, 316b are directed to the pin connector 322, as opposed to the secondary lead output connector 324, and specifically to contacts 304a and 304b, respectively. Contacts 318a-318f of the pin connector 322 do not receive their own stimulation signals from conductors of the lead body of input cable 206. However, the pin 226 includes a first contact 310a and a second contact 310b. The first contact 310a bridges together the contact 304a with the contacts 318a-318c. Therefore, the stimulation signal provided from conductor 316a is distributed to contacts 304a and 318a-318c. As shown, contacts 304a and 318a-318c are connected to contacts 306a-306d of the secondary lead connector 324, and these contacts 306a-306d are in turn physically connected to the contacts 312a-312d of the secondary lead 114. So, ultimately, electrodes of the secondary lead 114 that are connected to the contacts 312a-312d provide the same stimulation signal of conductor 316a to the tissue.

Similarly, the second contact 310b bridges together the contact 304b with the contacts 318d-318f. Therefore, the stimulation signal provided from conductor 316b is distributed to contacts 304b and 318d-318f. As shown, contacts 304b and 318d-318f are connected to contacts 306e-306h of the secondary lead connector 324, and these contacts 306e-306h are in turn physically connected to the contacts 312e-312h of the secondary lead 114. So, ultimately, electrodes of the secondary lead 114 that are connected to the contacts 312e-312h provide the same stimulation signal of conductor 316b to the tissue. Note that the stimulation signal of conductor 316b may be an opposite polarity and hence the return path for the stimulation signal of conductor 316a, or vice versa.

In order to produce a different stimulation pattern from the secondary lead 114, the contact configuration of the pin 226 may be changed just by removing the pin 226 and inserting a different pin with a different contact configuration. The different contact configuration bridges together the contacts of the pin connector 322, and hence the contacts of the secondary lead connector 324 in a different manner. Examples of different pin contact configurations are discussed below.

Figure 3B:
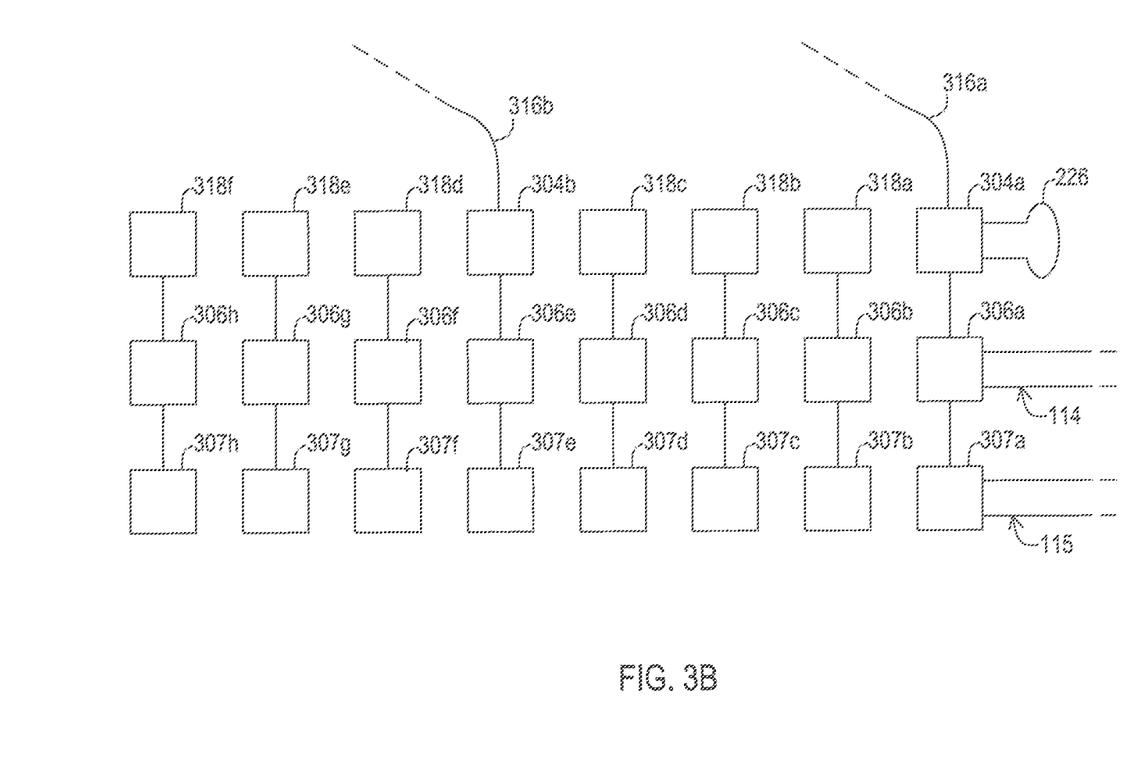
FIG. 3B shows a variation of the example of FIG. 3A where an additional secondary lead is included.

FIG. 3B shows an adaptation to the adapter configuration of FIG. 3A. Here, there are two secondary lead connectors, each having the appropriate number of contacts. In this example, the third lead 115 for the adapter, which is the second secondary lead, is wired in parallel with the first secondary lead 114. Contact 306a is electrically connected to contact 307a and so on. Thus, the second secondary lead 115 provides the same customized stimulation pattern as that being provided by the first secondary lead 114.

Figure 4:
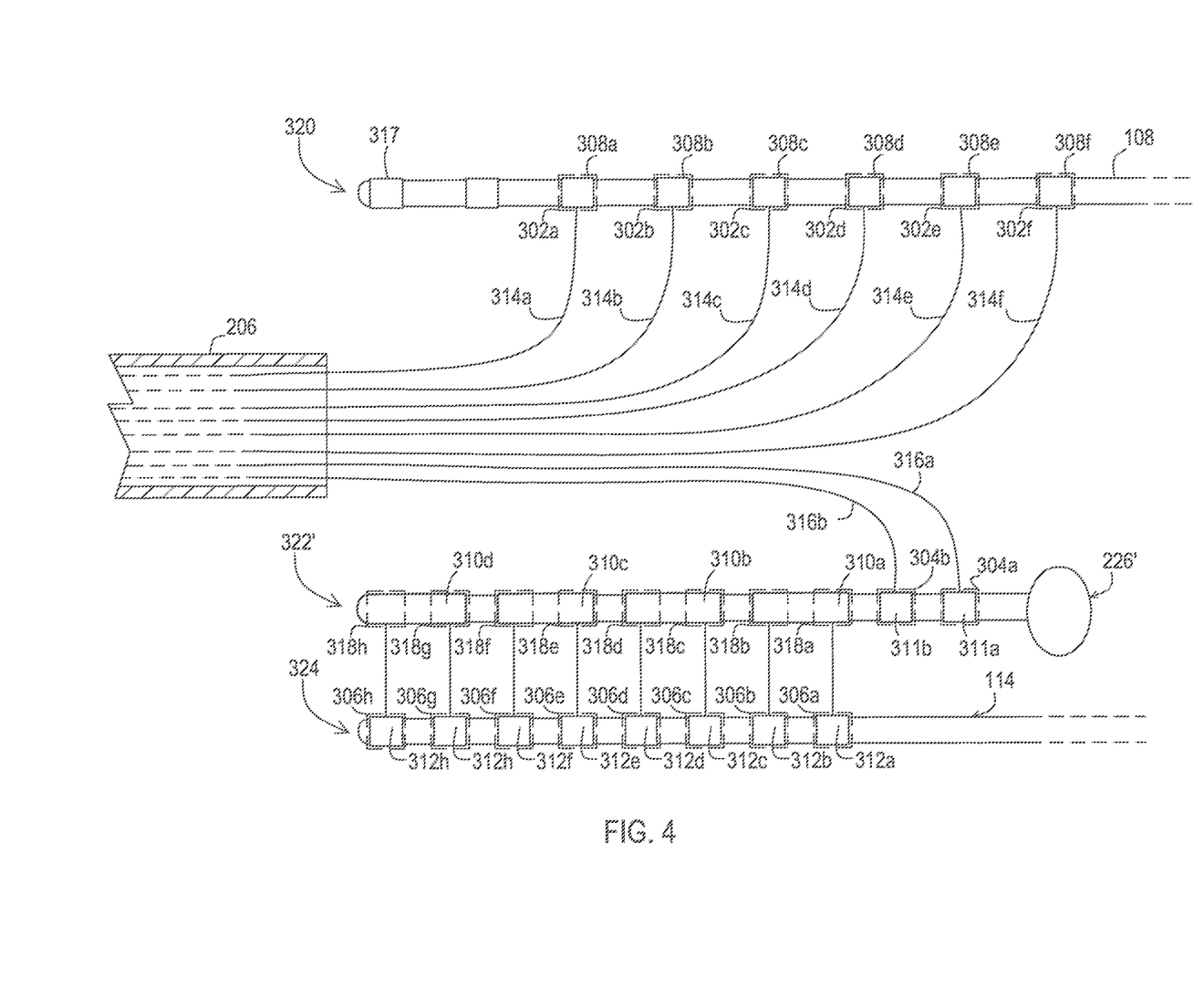
FIG. 4 shows a second example of stimulation pathways established by embodiments of a medical system lead adapter.

FIG. 4 shows another example of a different pin 226' providing a different structure that creates a different configuration for bridging together contacts for the secondary lead 114. Also, the pin connector 322' provides for two contacts 304a and 304b that are used only for receive the stimulation signals and are not used for direct connection to contacts of the secondary lead connector 324, which provides additional flexibility to increase the number of stimulation patterns that may be achieved.

Initially, the first set of conductors 314a-314f are directed from the lead body of input cable 206 of the adapter 104 to a set of electrical contacts 302a-302f of a primary lead connector 320 within the adapter 104. The primary lead 108 then has a set of electrical contacts 308a-308f that physically contact the electrical contacts 302a-302f to receive stimulation signals as in FIG. 3A. Also in this particular example, the primary lead 108 has two additional contacts 317 which are left unconnected.

The conductors 316a, 316b of a second set are directed to the pin connector 322', as opposed to the secondary lead connector 324, and specifically to contacts 304a and 304b, respectively. Contacts 318a-318h of the pin connector 322' do not receive their own stimulation signals from conductors of the lead body of input cable 206. However, the pin 226' includes a first contact 311a and a second contact 311b. The first contact 311a is internally connected to contacts 310a and 310c, and these contacts bridges together the contact 304a with the contacts 318a, 318b, 318e, and 318f. Therefore, the stimulation signal provided from conductor 316a is distributed to contacts 304a and 318a, 318b, 318e, and 318f. As shown, contacts 318a, 318b, 318e, and 318f are connected to contacts 306a, 306b, 306e, and 306f of the secondary lead connector 324, and these contacts 306a, 306b, 306e, and 306f are in turn physically connected to the contacts 312a, 312b, 312e, and 312e of the secondary lead 114. So, ultimately, electrodes of the secondary lead 114 that are connected to the contacts 312a, 312b, 312e, and 312e provide the same stimulation signal of conductor 316a to the tissue.

Similarly, the second contact 311b is internally connected to contacts 310b and 310d, and these contacts bridges together the contact 304b with the contacts 318c, 318d, 318g, and 318h. Therefore, the stimulation signal provided from conductor 316b is distributed to contacts 304b and 318c, 318d, 318g, and 318h. As shown, contacts 318c, 318d, 318g, and 318h are connected to contacts 306c, 306d, 306g, and 306h of the secondary lead connector 324, and these contacts 306c, 306d, 306g, and 306h are in turn physically connected to the contacts 312c, 312d, 312g, and 312h of the secondary lead 114. So, ultimately, electrodes of the secondary lead 114 that are connected to the contacts 312c, 312d, 312g, and 312h provide the same stimulation signal of conductor 316b to the tissue. Note that the stimulation signal of conductor 316b may again be an opposite polarity and hence the return path for the stimulation signal of conductor 316a, or vice versa.

Figure 5:
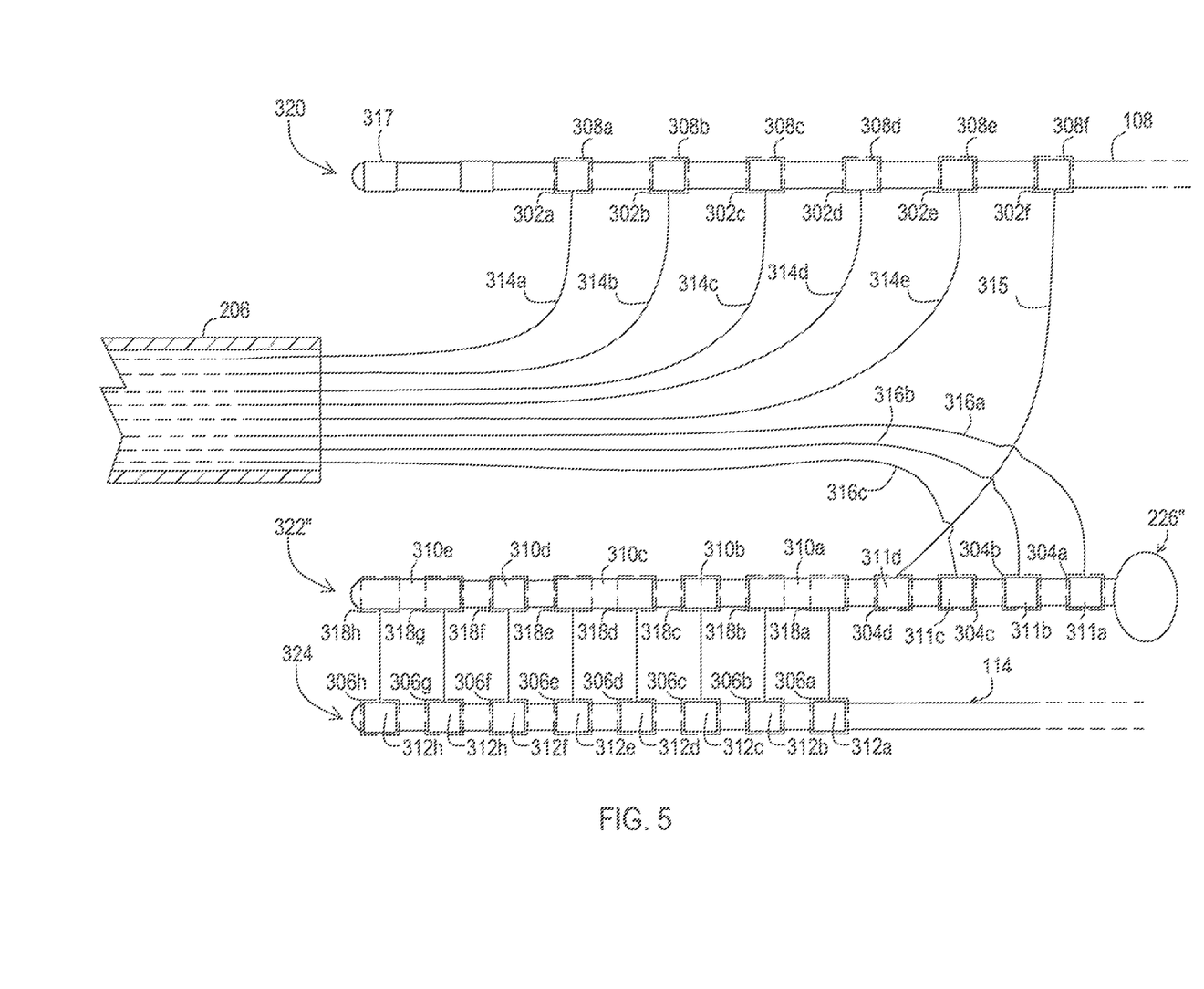
FIG. 5 shows a third example of stimulation pathways established by embodiments of a medical system lead adapter.

FIG. 5 shows another example of a different pin 226" providing a different structure that creates a different configuration for bridging together contacts for the secondary lead 114. Also, the pin connector 322" also provides for the two contacts 304a and 304b that are used only for receiving the stimulation signals and are not used for direct connection to contacts of the secondary lead connector 324, which again provides additional flexibility to increase the number of stimulation patterns that may be achieved. Additionally, in this embodiment of the pin connector 322", two additional contacts 304c and 304d are included. This provides additional flexibility in that these contacts are used to selectively distribute an additional conductor 316c to the secondary lead 114 or to the primary lead 108.

Initially, the first set of conductors 314a-314e are directed from the lead body of input cable 206 of the adapter 104 to a set of electrical contacts 302b-302f of a primary lead connector 320 within the adapter 104. The primary lead 108 then has a set of electrical contacts 308a-308f that physically contact the electrical contacts 302a-302f to receive stimulation signals as in FIG. 3A. Also in this particular example, the primary lead 108 has two additional contacts 317 which are left unconnected.

The second set of conductors 316a, 316b, and 316c are directed to the pin connector 322", as opposed to the secondary lead connector 324, and specifically to contacts 304a, 304b, and 304c respectively. Contacts 318a-318h of the pin connector 322" do not receive their own stimulation signals from conductors of the lead body of input cable 206. However, the pin 226" of this example includes a first contact 311a, second contact 311b, and third contact 311c. In this example, the first contact 311a is internally connected to contacts 310a, 310c, and 310e. These contacts bridge together the contact 304a with the contacts 318a, 318b, 318d, 318e, 318g, and 318h. Therefore, the stimulation signal provided from conductor 316a is distributed to contacts 304a, 318a, 318b, 318d, 318e, 318g, and 318h. As shown, contacts 318a, 318b, 318d, 318e, 318g, and 318h are connected to contacts 306a, 306b, 306d, 306e, 306g, and 306h of the secondary lead connector 324, and these contacts 306a, 306b, 306d, 306e, 306g, and 306h are in turn physically connected to the contacts 312a, 312l, 312d, 312e, 312g, and 312h of the secondary lead 114. So, ultimately, electrodes of the secondary lead 114 that are connected to the contacts 312a, 312b, 312d, 312e, 312g, and 312h, and 312e provide the same stimulation signal of conductor 316a to the tissue.

Similarly, the second contact 311b is internally connected to contacts 310b and 310d. These contacts bridge together the contact 304b with the contacts 318c and 318f. Therefore, the stimulation signal provided from conductor 316b is distributed to contacts 304b, 318c, and 318f. As shown, contacts 318c and 318f are connected to contacts 306c and 306f of the secondary lead connector 324, and these contacts 306c and 306f are in turn physically connected to the contacts 312c and 312f of the secondary lead 114. So, ultimately, electrodes of the secondary lead 114 that are connected to the contacts 312c and 312f provide the same stimulation signal of conductor 316b to the tissue. Note that the stimulation signal of conductor 316b may again be an opposite polarity and hence the return path for the stimulation signal of conductor 316a, or vice versa.

The third contact 311c of the pin 226" may be either internally connected to the fourth contact 311d or be internally connected to one of the other contacts 310a-310e in place of the connection from the contact 311a or 311b. By having a pin 226" that internally connects the contact 311c with the contact 311d, the pin 226" thereby electrically connects the contact 304c receiving the stimulation signal of the conductor 316c with the contact 304d which is connected to a conductor 315. The contact 304d thereby serves as a jumper contact to jumper the signal from contact 304c to the conductor 315. The conductor 315 is connected to one of the contacts of the primary lead connector 320 such as the contact 302f which connects to the primary lead contact 308f. Thus, in this case, the primary lead continues to receive six individual stimulation signals while the secondary lead 114 receives two individual stimulation signals.

Where the pin 226" internally connects the contact 311c to another contact besides 311d, then the conductor 315 is not driven. Therefore, the primary lead 108 is driven by only five individual stimulation signals while the secondary lead is driven by three individual stimulation signals. Having three individual stimulation signals may allow additional customization for the secondary lead 114, such as driving one or more electrodes with a different voltage and/or frequency from conductor 316c than is being driven from the conductor 316a or 316b.

Figure 6:
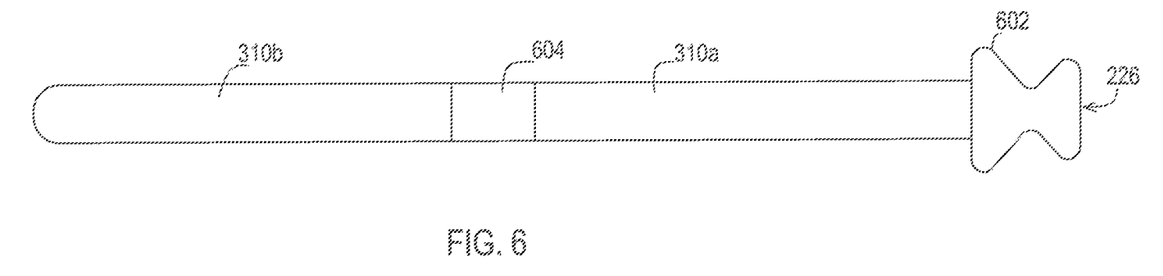
FIG. 6 shows a first example of a pin used to establish a particular stimulation pattern fir a secondary lead.

FIG. 6 shows an example of the pin 226. In this example, the pin 226 includes a nonconductive handle 602. The pin also includes a first contact 310a and a second contact 310b like that shown in FIG. 3A. The contacts 310a and 310b receive stimulation signals and then bridge those signals to other contacts of the pin connector as discussed above. The first contact and the second contact are electrically isolated by an intervening nonconductive section 604. The nonconductive sections may be constructed from biocompatible materials such as polyurethane and the like. The contacts 310a and 310b may be constructed of biocompatible materials such as stainless steel.

Figure 7A:
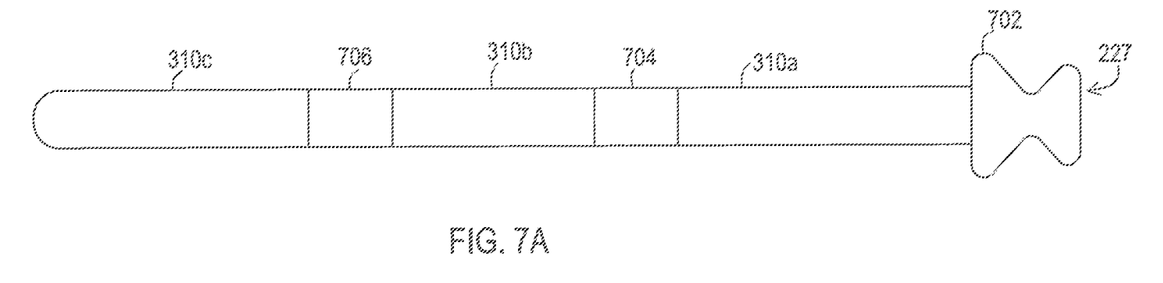
FIG. 7A shows a second example of a pin used to establish a particular stimulation pattern for a secondary lead.
Figure 7B:
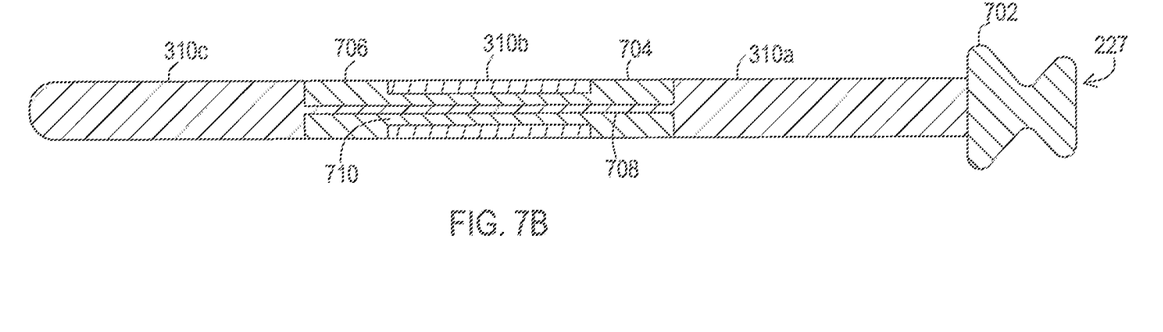
FIG. 7B shows a cross-sectional view of the second example of FIG. 7A.

FIG. 7A shows another example of a pin 227. In this example, the pin 227 includes a nonconductive handle 702 as well as a first contact 310a, a second contact 310b, and a third contact 310c. These contacts are separated by two nonconductive sections 704, 706.

Where each contact 310a, 310b, and 310c receives stimulation from a dedicated conductor of the input cable 206 of the adapter 104, such as from conductors 316a, 316b, and 316c of FIG. 5, then no internal connectivity among the contacts 310a, 310b, and 310c is provided. However, where only two dedicated conductors 316a and 316b are providing stimulation signals to the secondary lead 114, then the pin 227 is provided with internal connectivity to bridge two of the contacts together. FIG. 7B shows a cross-sectional view of a pin 227 providing such internal connectivity.

As shown in FIG. 7B, the contact 310a is bridged to the contact 310c by an internal conductor 708. The internal conductor 708 is surrounded by a nonconductor 710 extending between the nonconductive sections 704 and 706. Thus, a stimulation signal such as that of conductor 316a is provided to the contact 310a through a corresponding pin connector contact but is also provided to the contact 310c via the internal conductor 708. Meanwhile, another stimulation signal such as that of conductor 316b is provided to the contact 310b.

Figure 8A:
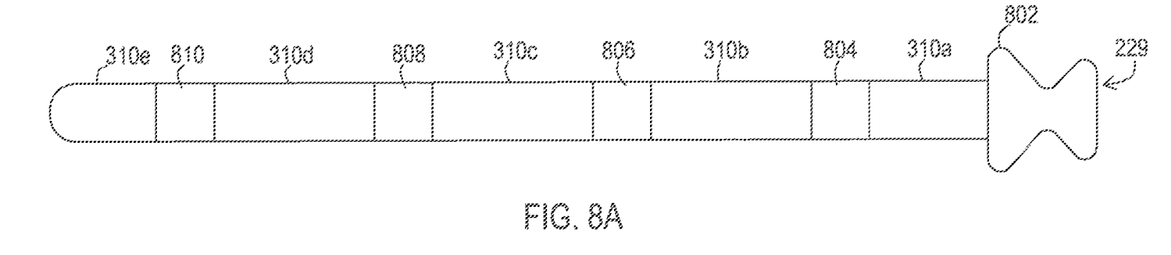
FIG. 8A shows a third example of a pin used to establish a particular stimulation pattern for a secondary lead.

FIG. 8A shows another example of a pin 229 with additional internal connectivity for a more complicated stimulation pattern. In this example, the pin 229 includes a nonconductive handle 802 as well as a first contact 310a, a second contact 310b, a third contact 310c, a fourth contact 310d, and a fifth contact 310e. These contacts are separated by four nonconductive sections 804, 806, 808, and 810.

Figure 8B:
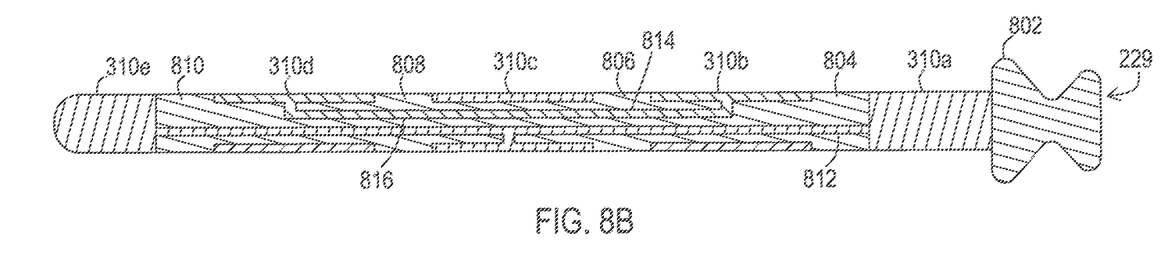
FIG. 8B shows a cross-sectional view of the second example of FIG. 8A.

In this example, only two dedicated conductors 316a and 316b are providing stimulation signals to the secondary lead 114. Therefore, the pin 229 is provided with internal connectivity to bridge two of the contacts together. FIG. 8B shows a cross-sectional view of the pin 229 providing such internal connectivity.

As shown in FIG. 8B, the contact 310a is bridged to the contact 310c and the contact 310e by an internal conductor 812. The internal conductor 812 is surrounded by a nonconductor 816 extending between the nonconductive sections 804 and 810. Thus, a stimulation signal such as that of conductor 316a is provided to the contact 310a through a corresponding pin connector contact but is also provided to the contact 310c and the contact 310e via the internal conductor 812. Meanwhile, another stimulation signal such as that of conductor 316b is provided to another contact, such as the contact 310b for example. The contact 310b is bridged to the contact 310d via an internal conductor 814. Thus, a stimulation signal such as that of conductor 316b is provided to the contact 310b through a corresponding pin connector contact but is also provided to the contact 310d via the internal conductor 814.

It will be appreciated that there are many potential pin conductor configurations, particularly when utilizing internal conductors to bridge together contacts of the pin. In particular, the pins 226' and 226" utilize such internal conductors like those shown in FIG. 8B to bridge the pin contacts 311a and 311b to the various other contacts of the pin. It will also be appreciated that the particular pin contact that receives the stimulation signal from a pin connector contact may vary from that discussed above in FIGS. 3A-8B.

Table 1 below provides some illustrative examples of stimulation signal configurations that may be achieved for the secondary lead 114 using different pins within the adapter 104.

TABLE 1

Stimulation Pattern Examples

| 312h | 312g | 312f | 312e | 312d | 312c | 312b | 312a |
|------|------|------|------|------|------|------|------|
| −    | −    | −    | −    | +    | +    | +    | +    |
| +    | +    | −    | −    | −    | −    | +    | +    |
| −    | +    | −    | +    | −    | +    | −    | +    |
| +    | −    | −    | +    | +    | −    | −    | +    |
| +    | −    | −    | −    | −    | −    | −    | +    |
| −    | −    | +    | +    | +    | +    |      |      |
| −    | −    | −    | +    | +    | +    |      |      |
|      |      | −    | +    | +    |      |      |      |
| −    | −    | −    | +    | +    | +    |      |      |

Figure 9:
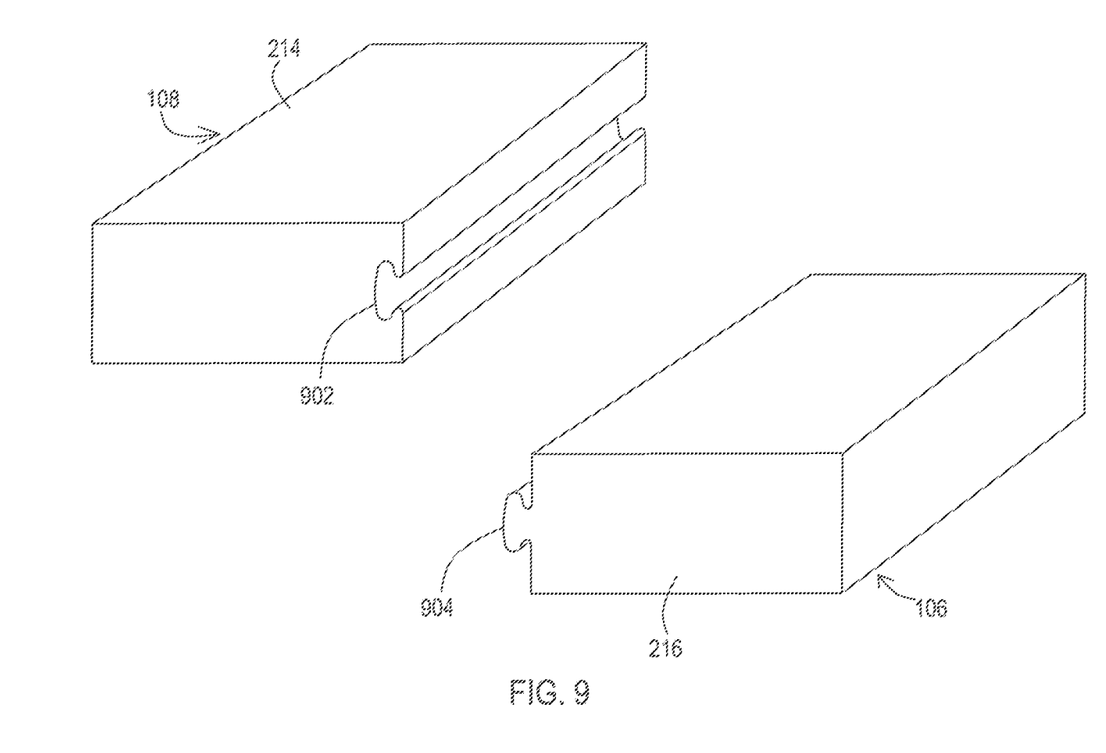
FIG. 9 shows two adapters having complementary features to physically join the two adapters together.

FIG. 9 shows an attachment feature that the housings 214, 216 may include to affix one housing to the other for purposes of implantation. For example, one housing 214 may have a groove 902 as an attachment feature while the other housing includes a tongue 904 as an attachment feature that slides within the groove 902. It will be appreciated that various types of features other than the tongue and groove configuration may also be used to affix the housings together. Furthermore, it will be appreciated that a given adapter housing may have a multiple attachment features, such as a tongue 904 on one side and a groove 902 on an opposing side.

While embodiments have been particularly shown and described, it will be understood by those skilled in the art that various other changes in the form and details may be made therein without departing from the spirit and scope of the invention.

What is claimed is:

1. A medical system lead adapter, comprising:
    an input cable having a plurality of electrical conductors that establish an electrical connection with a first plurality of electrical contacts of a medical device;
    a first output connector that receives a proximal end of a first medical lead, the first output connector having a second plurality of electrical contacts that establish a connection with respective contacts of a third plurality of electrical contacts of the first medical lead, the second plurality of electrical contacts of the first output connector being electrically connected to respective conductors of a first set of the plurality of electrical conductors of the input cable;
    a second output connector that receives a proximal end of a second medical lead, the second output connector having a fourth plurality of electrical contacts that establish a connection with respective contacts of a fifth plurality of electrical contacts of the second medical lead;
    a pin connector having a sixth plurality of electrical contacts, wherein at least some of the sixth plurality of electrical contacts of the pin connector are electrically connected to respective contacts of the fourth plurality of electrical contacts of the second output connector, and wherein a subset of the sixth plurality of electrical contacts of the pin connector are electrically connected to respective conductors of a second set of the plurality of electrical conductors; and a pin present within the pin connector, the pin including a first pin conductor that electrically bridges together one or more first electrical contacts of the pin connector not in the subset of the sixth plurality of electrical contacts to a primary electrical contact from the subset of the sixth plurality of electrical contacts of the pin connector, the pin further including a second pin conductor that electrically bridges together one or more second electrical contacts of the pin connector not in the subset of the sixth plurality of electrical contacts to a secondary electrical contact from the subset of the sixth plurality of electrical contacts of the pin connector.

2. The medical system lead adapter of claim 1, wherein the one or more first electrical contacts of the pin connector not in the subset comprises a plurality of electrical contacts of the pin connector not in the subset.

3. The medical system lead adapter of claim 2, wherein the one or more second electrical contacts of the pin connector not in the subset comprises a plurality of electrical contacts of the pin connector not in the subset.

4. The medical system lead adapter of claim 1, further comprising a housing that receives the input cable and that positions the first output connector, the second output connector, and the pin connector.

5. The medical system lead adapter of claim 4, wherein the housing includes an attachment feature that mates to an attachment feature of another housing.

6. The medical system lead adapter of claim 1, further comprising a third output connector that receives a proximal end of a third medical lead, the third output connector having a seventh plurality of electrical contacts that establish a connection with respective contacts of an eighth plurality of contacts of the third medical lead.

7. The medical system lead adapter of claim 1, wherein the electrical contacts of the subset of the sixth plurality of electrical contacts of the pin connector are electrically connected to respective contacts of the fourth plurality of electrical contacts of the second output connector.

8. The medical system lead adapter of claim 1, wherein the electrical contacts of the subset of the sixth plurality of electrical contacts of the pin connector are not electrically connected to respective contacts of the fourth plurality of electrical contacts of the second output connector.

9. The medical system lead adapter of claim 1, wherein the pin connector further comprises a jumper contact that is electrically connected to another electrical contact of the first output connector that is not electrically connected to the electrical conductors of the input cable, and wherein the pin further includes a third pin conductor that bridges the jumper contact to an electrical contact of the subset of the sixth plurality of electrical contacts of the pin conductor that is electrically connected to a respective conductor of the electrical conductors.

10. A medical system, comprising:
a medical device having a first plurality of electrical contacts that are given electrical potentials to provide therapy; and
a medical system lead adapter comprising:
an input cable having a plurality of electrical conductors that establish an electrical connection with the first plurality of electrical contacts of the medical device;
a first output connector that receives a proximal end of a first medical lead, the first output connector having a second plurality of electrical contacts that establish a connection with respective contacts of a third plurality of electrical contacts of the first medical lead, the second plurality of electrical contacts of the first output connector being electrically connected to respective conductors of a first set of the plurality of electrical conductors of the input cable;
a second output connector that receives a proximal end of a second medical lead, the second output connector having a fourth plurality of electrical contacts that establish a connection with respective contacts of a fifth plurality of electrical contacts of the second medical lead;
a pin connector having a sixth plurality of electrical contacts, wherein at least some of the sixth plurality of electrical contacts of the pin connector are electrically connected to respective contacts of the fourth plurality of electrical contacts of the second output connector, and wherein a subset of the sixth plurality of electrical contacts of the pin connector are electrically connected to respective conductors of a second set of the plurality of electrical conductors; and
a pin present within the pin connector, the pin including a first pin conductor that electrically bridges together one or more first electrical contacts of the pin connector not in the subset of the sixth plurality of electrical contacts to a primary electrical contact from the subset of the sixth plurality of electrical contacts of the pin connector, the pin further including a second pin conductor that electrically bridges together one or more second electrical contacts of the pin connector not in the subset of the sixth plurality of electrical contacts to a secondary electrical contact from the subset of the sixth plurality of electrical contacts of the pin connector.

11. The medical system of claim 10, wherein the one or more first electrical contacts of the pin connector not in the subset comprises a plurality of electrical contacts of the pin connector not in the subset.

12. The medical system of claim 11, wherein the one or more second electrical contacts of the pin connector not in the subset comprises a plurality of electrical contacts of the pin connector not in the subset.

13. The medical system of claim 10, wherein the medical system lead adapter further comprises a housing that receives the input cable and that positions the first output connector, the second output connector, and the pin connector.

14. The medical system of claim 13, wherein the housing includes an attachment feature that mates to an attachment feature of another housing.

15. The medical system any of claim 10, further comprising a third output connector that receives a proximal end of a third medical lead, the third output connector having a seventh plurality of electrical contacts that establish a connection with respective contacts of an eighth plurality of contacts of the third medical lead.

16. The medical system of claim 10, wherein the electrical contacts of the subset of the sixth plurality of electrical contacts of the pin connector are electrically connected to respective contacts of the fourth plurality of electrical contacts of the second output connector.

17. The medical system of claim 10, wherein the electrical contacts of the subset of the sixth plurality of electrical contacts of the pin connector are not electrically connected to respective contacts of the fourth plurality of electrical contacts of the second output connector.

18. The medical system of claim 10, wherein the pin connector further comprises a jumper contact that is electrically connected to another electrical contact of the first output connector that is not electrically connected to the electrical conductors of the input cable, and wherein the pin further includes a third pin conductor that bridges the jumper contact to an electrical contact of the subset of the sixth plurality of electrical contacts of the pin conductor that is electrically connected to a respective conductor of the electrical conductors.

19. A method of providing stimulation, comprising:
   directing a first set of stimulation signals to respective electrical contacts of a first plurality of electrical contacts of a first lead; and
   directing a second set of stimulation signals to electrical contacts of a second plurality of electrical contacts of a second lead by selectably bridging the second set of stimulation signals to respective electrical contacts of the second plurality of electrical contacts of the second lead, wherein directing the second set of stimulation signals to electrical contacts of the second plurality of electrical contacts of the second lead comprises:
      receiving the second set of stimulation signals via an input cable; and
      directing each stimulation signal of the second set of stimulation signals to a respective electrical contact of a third plurality of electrical contacts of a pin connector via a pin, wherein:
         the pin comprises a first pin conductor that bridges a first stimulation signal of the second set of stimulation signals to a first set of the third plurality of electrical contacts of the pin connector and a second pin conductor that bridges a second stimulation signal of the second set of stimulation signals to a second set of the third plurality of electrical contacts of the pin connector, and
         the third plurality of electrical contacts of the pin connector are electrically connected to respective electrical contacts of the second plurality of electrical contacts of the second lead.

20. The method of claim 19, wherein directing the second set of stimulation signals to electrical contacts of the second plurality of electrical contacts of the second lead by selectably bridging the second set of stimulation signals to respective electrical contacts of the second plurality of electrical contacts of the second lead comprises inserting the pin into the pin connector.

21. The method of claim 19, wherein the pin is a first pin, and wherein the method further comprises:
   removing the first pin from the pin connector; and
   inserting a second pin into the pin connector, wherein the second pin comprises a second contact configuration different than a first contact configuration of the first pin.

* * * * *